United States Patent [19]

Brickl et al.

[11] 4,229,479
[45] Oct. 21, 1980

[54] FLUORACYLRESORCINOLS AS INGREDIENTS IN PHARMACEUTICAL, COSMETIC AND PESTICIDAL COMPOSITIONS

[75] Inventors: Rolf Brickl; Hans Eberhardt; Karl-Richard Appel, all of Biberach; Uwe Lechner, Ummendorf; Walter Merk, Biberach, all of Fed. Rep. of Germany

[73] Assignee: Boehringer Ingelheim GmbH, Ingelheim am Rhein, Fed. Rep. of Germany

[21] Appl. No.: 937,991

[22] Filed: Aug. 30, 1978

Related U.S. Application Data

[63] Continuation of Ser. No. 786,266, Apr. 11, 1977, abandoned.

[30] Foreign Application Priority Data

Apr. 14, 1976 [DE] Fed. Rep. of Germany ....... 2616478

[51] Int. Cl.³ .................... A01N 35/00; A61K 31/12
[52] U.S. Cl. .................................. 424/331; 71/122; 424/DIG. 4; 424/45; 424/47
[58] Field of Search ............................... 424/331

[56] References Cited

U.S. PATENT DOCUMENTS

| 2,283,471 | 5/1942 | Swaine | 424/331 |
| 3,021,256 | 2/1962 | Bollenbach et al. | 424/331 |
| 3,184,379 | 5/1965 | Lukes et al. | 424/331 |

OTHER PUBLICATIONS

Whalley; C.A. vol. 46, (1952) pp. 9536-9537.
Whalley; J. Chem. Soc. 73 pp. 665-671, 1951.

*Primary Examiner*—Allen J. Robinson
*Attorney, Agent, or Firm*—Hammond & Littell, Weissenberger & Muserlian

[57] ABSTRACT

Pharmaceutical, cosmetic and pesticidal compositions containing a trifluoroacetyl-resorcinol of the formula

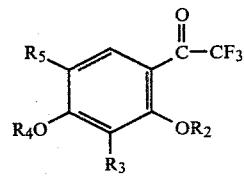

wherein
$R_2$ and $R_4$, which may be identical to or different from each other, are each hydrogen or methyl, and
$R_3$ and $R_5$, which may be identical to or different from each other, are each hydrogen or ethyl.

1 Claim, No Drawings

FLUORACYLRESORCINOLS AS INGREDIENTS IN PHARMACEUTICAL, COSMETIC AND PESTICIDAL COMPOSITIONS

This is a continuation of copending application Ser. No. 786,266 filed Apr. 11, 1977, now abandoned.

This invention relates to novel pharmaceutical, cosmetic and pesticidal compositions containing a trifluoroacetyl-resorcinol.

More particularly, the present invention relates to novel pharmaceutical, cosmetic and pesticidal compositions containing a trifluoroacetyl-resorcinol of the formula

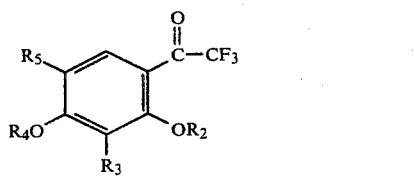

(I)

wherein
$R_2$ and $R_4$, which may be identical to or different from each other, are each hydrogen or methyl, and
$R_3$ and $R_5$, which may be identical to or different from each other, are each hydrogen or ethyl.

These compounds are chemically described by W. B. Whalley in J. Chem. Soc. 73, pages 665 et seq. (1951); disclosures with regard to biological activities have not been made.

We have discovered that these compounds surprisingly exhibit good inhibitory effects on bacteria and fungi, various key enzymes of carbohydrate metabolism and on mitosis in and on the skin.

The substituted trifluoroacetyl-resorcinols of the formula I may be prepared as follows:

Method A

By acylation of resorcinol or a derivative thereof of the formula

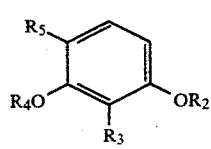

(II)

wherein $R_2$ to $R_5$ have the meanings hereinbefore defined, by means of a carboxylic acid or a derivative thereof of the formula $CF_3-COY$ (III)

wherein Y is hydroxyl, amino, acyloxy, alkoxy or halogen, in the presence of a Friedel-Crafts catalyst and a solvent at temperatures between −80° C. and the boiling point of the solvent, but preferably at room temperature.

Suitable solvents include aliphatic hydrocarbons, carbon disulfide, halogenated, especially chlorinated aliphatic hydrocarbons, ether, aromatic hydrocarbons such as benzene, toluene, chlorobenzene and dichlorobenzene, but also inorganic solvents such as phosphorus oxychloride, polyphosphoric acid, phosphoric acid and sulfuric acid.

Suitable catalysts are Lewis-acids such as anhydrous aluminum chloride, iron(III)chloride, zinc chloride, boron trifluoride or the ethoxides thereof, tin(IV)chloride, antimony-tri- or penta-halides, phosphorus-tri- or penta-halides, phosphorus pentoxide or inorganic acids such as hydrochloric acid, hydrofluoric acid, sulfuric acid, polyphosphoric acid or chlorosulfonic acid, or strong organic acids such as p-toluenesulfonic acid.

Method B

By reaction of resorcinol or a derivative thereof of the formula

(II)

wherein $R_2$ through $R_5$ have the meanings previously defined, under the conditions of the ketone synthesis according to Hösch with a perfluorocarboxylic acid nitrile of the formula $CF_3-CN$ (IV)

The reaction is carried out at temperatures between −80° C. and the boiling point of the solvent in the presence of a Lewis-acid as a catalyst and an organic solvent, preferably at −20° C. to +80° C.

Suitable Lewis-acids are, among others, anhydrous aluminum chloride, zinc chloride especially in the presence of hydrochloric acid, furthermore iron(III)chloride and tin(IV)chloride, titanium tetrachloride, chromium trichloride, boron triflouride, p-toluenesulfonic acid, phosphoric acid, polyphosphoric acid or hydrofluoric acid. Examples of suitable solvents are ether, chlorobenzene, nitrobenzene, xylene and phosphorus oxychloride.

The starting compounds of the formula II are known from the literature.

The following examples illustrate the preparation of compounds embraced by formula I:

EXAMPLE 1

2,4-Dihydroxy-trifluoroacetophenone by method A 110 gm of resorcinol (1 mol) were suspended in 3 liters of ethylene chloride, 300 gm (2.25 mols) of aluminum chloride were added to the suspension in small amounts at about 20° C. while stirring, and subsequently 260 gm (1.2 mols) of trifluoroacetic acid anhydride were added dropwise at 15°–20° C. over a period of about 1½ hours, while the mixture was cooled on an ice water bath. Subsequently, the mixture was stirred for 3 hours more and was then allowed to stand for 1 to 2 days at room temperature. For decomposition, the mixture was poured over about 2.5 kg of ice while stirring (exterior cooling, temperature was not allowed to rise above 25° C.). The organic phase was separated, and the aqueous phase was washed three times with 500 ml each of ethylene chloride. The combined organic phases were washed with 1 liter of water, dried over calcium chloride and evaporated. The residue was recrystallized from heptane, yielding 175 gm (84% of theory) of the compound of the formula

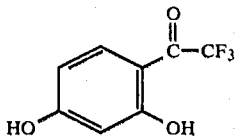

which had a melting point of 103° C.

The following compounds were prepared in analogous manner:
(a) 2,4-Dihydroxy-3-ethyl-trifluoroacetophenone, m.p. 139° C., from 2-ethyl-resorcinol in ethylene chloride; yield: 85% of theory.
(b) 2,4-Dihydroxy-5-ethyl-trifluoroacetophenone, m.p. 99° C., from 4-ethyl-resorcinol in ethylene chloride; yield: 77% of theory.
(c) 2,4-Dimethoxy-trifluoroacetophenone, m.p. 52° C., from resorcinol dimethyl ether in ethylene chloride; yield: 75% of theory.
(d) 2,4-Dimethoxy-3-ethyl-trifluoroacetophenone, m.p. 128° C., from 2-ethyl-resorcinol dimethyl ether in ethylene chloride; yield:76% of theory.
(e) 2,4-Dimethoxy-5-ethyl-trifluoroacetophenone, m.p. 130° C., from 4-ethyl resorcinol dimethyl ether in ethylene chloride; yield: 79% of theory.

As indicated above, we have discovered that the compounds of the formula I have useful pharmacological properties: in particular, they are active against bacteria, dermatophytes, yeasts and molds; they have an inhibitory effect on various key enzymes of carbohydrate metabolism and on cell cultures, thus they delay accelerated processes of mitosis in and on the skin. Therefore, they are suitable for the treatment of acne, dandruff, bacterial skin infections, mycoses, psoriasis, ichthyosis and hyperkeratotic states of the skin.

The compounds of the formula I are especially suitable for incorporation into cosmetic preparations, such as foam aerosols, powder sprays, powders, shampoos, creams, ointments, gels, detergents such as cleansing lotions, face lotions or hair tonics. The compounds here serve as disinfectants or as preservatives; additionally they normalize hyperkeratosis of the skin and counteract the formation of dandruff in hair tonics.

For example, the following substances were tested for their inhibitory effects on bacteria and fungi, cell cultures and enzyme activities:

| | |
|---|---|
| 2,4-Dihydroxy-trifluoroacetophenone | = A |
| 5-Ethyl-2,4-dihydroxy-trifluoroacetophenone | = B |
| 3-Ethyl-2,4-dihydroxy-trifluoroacetophenone | = C |
| 2,4-Dimethoxy-trifluoroacetophenone | = D |

The inhibitory effect on bacteria and fungi was examined according to the serial dilution test and the agar diffusion test (hole-test). As bacteria were used: *Staphylococcus aureus* SG 511, *Streptococcus aronson*, *Streptococcus pyogenes* AT CC 86 68; as fungi: *Candida albicans* AT CC 10231, *Trichophyton mentagrophytes* AT CC 9129 and *Aspergillus niger*.

Serial dilution test

Nutrient media
1. Meat extract broth: for *St. aureau* SG 511
Recipe:
| | |
|---|---|
| Peptone | 10 gm |
| Meat extract | 8 gm |
| Sodium chloride | 3 gm |
| Sec. sodium phosphate (Na$_2$HPO$_4$) | 2 gm |
| ad 1,000 ml of distilled water | (pH 7.2–7.4) |

Sterilization: 15 minutes at 120° C. in the autoclave
2. Glucose broth: for *Sc. Aronson* and *St. pyogenes*
For recipe see meat extract broth. After sterilization 1 weight per cent of glucose is added as a sterile 50% solution.
3. Sabouraud broth: for *C. alb.*, *Trich.mnt.*, *A. niger*

Recipe:
| | |
|---|---|
| Peptone from Casein | 10 gm |
| Glucose | 40 gm |
| Sodium chloride | gm |
| Sec. sodium phosphate (Na$_2$HPO$_4$) | 1 gm |
| ad 1,000 ml of distilled water | |

Sterilization: 5-14 10 minutes at 120° C.
a pH was not adjusted

Standardization of the density of microorganisms

The age of the primary cultures is 24 hr. for bacteria and 14 days for fungi. The standardization of the suspension of microorganisms is effected using a photometer according to Eppendorf (test tube φ 14 mm, filter 546 nm) and a suspension for comparison consisting of barium sulfate, this suspension being created by addition of 3.0 ml of 1% barium chloride solution to 97 ml of 1% sulfuric acid. After the standardization the bacteria were further diluted to a concentration of 1:1000 by means of sodium chloride solution, the fungi were used in an undiluted state.

Preparation of the substance concentration 40 mgm of the substance were put into a 10 ml measuring flask and filled up to the mark with the solvent (corresponds to a dilution of 1:250=4000 μg/ml). The further dilution series was standardized with distilled water or the respective solvent and the following substance concentrations were prepared: 1000; 250; 62.5 μg/ml.

Execution of the test

The tubes were filled with 4.9 ml of the corresponding liquid nutrient medium. Then 0.1 ml of the substance dilution prepared above was added to each tube, so that the mentioned final concentrations were present. Finally each tube was inoculated with 0.1 ml of the standardized suspension of microorganisms. Control tests merely using the solvent are to be carried out simultaneously.

Incubation

Bacteria were incubated at 37° C. for 18–20 hours and fungi at 27° C. for 7 days.

Evaluation

The measurement is carried out macroscopically defining the minimal inhibitory concentration (the lowest still microbiostatically effective concentration).

Agar diffusion test

Nutrient media
1. Meat extract agar: for *St. aureus* SG 511
Recipe
| | |
|---|---|
| Peptone | 10 gm |
| Meat extract | 8 gm |
| Sodium chloride | 3 gm |

| -continued | |
|---|---|
| Sec. sodium phosphate (Na$_2$HPO$_4$) | 2 gm |
| Pronagar | 15 gm |
| ad 1,000 ml of distilled water | (pH 7.2–7.4) |

Sterilization: 15 minutes at 120° C. in the autoclave
2. Glucose agar: for Sc. Aronson and St. pyogenes
For recipe see meat extract agar. After sterilization 1 weight per cent of glycose is addad as a sterile 50% solution.
3. Sabouraud agar: for C. alb., Trich. ment., A. niger

| Recipe: | |
|---|---|
| Peptone from Casein | 10 gm |
| Glucose | 40 gm |
| Sodium chloride | 1 gm |
| Sec. sodium phosphate (Na$_2$HPO$_4$) | 1 gm |
| Pronagar | 15 gm |
| ad 1,000 ml of distilled water | |
| Sterilization: 5–10 minutes at 120° C., a pH was not adjusted | |

Standardization of the density of microorganisms

The age of the primary cultures is 24 hours for bacteria and 14 days for fungi. The standardization of the suspension of microorganisms is effected using a photometer according to Eppendorf (test tube $\phi$ 14 mm, filter 546 nm) and a suspension for comparison consisting of barium sulfate, this suspension being created by addition of 3.0 ml of 1% barium chloride solution to 97 ml of 1% sulfuric acid. After the standardization St. aureus SG 511 was diluted 1:1000 and Sc. pyogenes and Aronson 1:100 by means of sodium chloride solution. The fungi were used in an undiluted state.

Preparation of the substance concentration 40 mgm of the substance were put into a 10 ml measuring flask and filled up to the mark with the solvent (corresponds to a dilution of 1:250=4000 μg/ml).
The dilutions to the concentrations under test were effected with distilled water or the respective solvent.

Execution of the test 19 ml of the nutrient medium were filled into sterile Petri dishes of a diameter of 8 cm and dried. Subsequently the agar plates were charged with 4 ml of seed agar. 100 ml of seed agar contain 1.25 ml of the suspension of microorganisms, an agar plate thus containing 0.05 ml of the suspension of microorganisms. After solidification of the agar, 5 holes of a diameter of 5 mm were punched into the plates and filled with 0.05 ml of the correspondingly concentrated substance solution.
Control tests merely using the solvent are to be carried out simultaneously.

Incubation

Bacteria were incubated at 37° C. for 18–20 hours and fungi at 27° C. for 7 days.

Evaluation

The diameter of the area of inhibition in mm was measured after having deducted the diameter of the hole. If instead of a growth free zone only considerably reduced growth has taken place, these values were put into brackets.

Serial dilution test for Corynebacterium acnes and Pityrosporum ovale

Nutrient medium

For Corynebacterium acnes: thioglycolate-broth
for Pityrosporum ovale: Littmann's broth
5 ml per tube.

Density of microorganisms

Suspension of microorganisms in 0.9% sodium chloride solution, standardized using a photometer according to Eppendorf by means of a suspension for comparison consisting of barium sulfate, for Corynbacterium acnes in a dilution of 1:100, for Pityrosporum ovale in an undiluted state. 0.1 ml of the suspensions was used per test tube. Dimethyl sulfoxide served as a solvent for the substances.

The suspension with Corynebacteria acnes was incubated at 37' C. for 48 hours, the suspension of Pityrosporum ovale at 27° C. for 7 days. The reading was effected by macroscopic evaluation of the growth of microorganisms and registration of the minimal inhibitory concentration.

Agar diffusion test for Pityrosporum ovale CBS 1878

Nutrient medium

Littmann's agar, 23 ml per Petri dish, diameter of dish 100 mm.

Density of microorganisms

Suspension of microorganisms in 0.9% sodium chloride solution, standardized using a photometer according to Eppendorf by means of a suspension for comparison consisting of barium sulfate. 0.05 ml per plate were used. The test substances were dissolved in dimethyl sulfoxide. The incubation time was 7 days at 27° C.; the area of inhibition in mm was measured, 0.05 ml of the solution of the substance were used for each punch-hole of a diameter of 6 mm.

The results of these tests are recorded in the following tables 1 and 2:

TABLE I

| | Activity on grampositive bacteria and Corynebacterium acnes: MIC-values in μ/ml | | | | | | |
|---|---|---|---|---|---|---|---|
| | Staphylococcus aureus SG 511 | | Streptococcus Aronson | | Streptococcus pyogenes | | Corynebacterium acnes |
| Substance | A.D.T. | S.D.T. | A.D.T. | S.D.T. | A.D.T. | S.D.T. | S.D.T. |
| A | 1000 | 80 | 1000 | 80 | nt | nt | 80 |
| B | 250 | 20 | 250 | 20 | 250 | 20 | 20 |
| C | 62.5 | 5 | 62.5 | 5 | 62.5 | 1.25 | 1.25 |
| D | >4000 | >80 | >4000 | >80 | >4000 | >80 | >80 | nt = not tested;
A.D.T. = agar diffusion test;
S.D.T. = serial dilution test;
MIC = minimal inhibitory concentration.

TABLE II

| | Activity on yeasts, dermatophytes, molds and *Pityrosporum ovale:* MIC-values in µg/ml | | | | | | | |
|---|---|---|---|---|---|---|---|---|
| | Candida albicans | | Trichophyton mentagrophytes | | Aspergillus niger | | Pityrosporum ovale | |
| Substance | A.D.T. | S.D.T. | A.D.T. | S.D.T. | A.D.T. | S.D.T. | A.D.T. | S.D.T. |
| A | 1000 | 80 | 250 | 20 | 250 | 20 | 1000 | 80 |
| B | 1000 | 20 | 250 | 5 | 250 | 20 | 1000 | 80 |
| C | 1000 | 20 | 62.5 | 1.25 | 1000 | 5 | 1000 | >80 |
| D | >4000 | >80 | >4000 | >80 | >4000 | >80 | >4000 | >80 |

Measurement of the inhibition of the glucose-6-phosphate-dehydrogenase.

The equilibrium was observed:

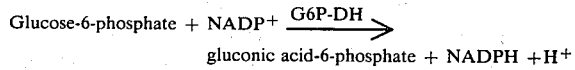

Glucose-6-phosphate + NADP+ $\xrightarrow{G6P-DH}$ gluconic acid-6-phosphate + NADPH +H+

The rate of formation of NADPH is a measure for the enzyme activity; it may be observed by means of the extinction increase at 340, 334 or 366 nm per unit of time.

Method 0.025 ml of glucose-6-phosphate-dehydrogenase (Boehringer Mannheim) were filled up to 10 ml of distilled water (solution I). 100 mgm of nicotinamide-adenine-dinucleotide-phosphate were dissolved in 13 ml of distilled water (solution II). 47.2 mgm of glucose-6-phosphate were dissolved in further 10 ml of distilled water (solution III). Simultaneously a buffer solution (solution IV) was prepared as follows:

0.28 gm of triethanolamine-hydrochloride and 1.461 gm of ethylene diaminotetraacetic acid-disodium salt were dissolved in 1 liter of distilled water and adjusted to a pH of 7.6 with sodium hydroxide solution. The substance under test was dissolved in dimethyl formamide or ethanol (solution V). Tested concentrations: 50; 25; 12.5; 6.25; 3.125; 1.56 and 0.78 µg/ml.

Determination of immediate inhibition 0.1 ml of solution I, 0.1 ml of solution II, 2.67 ml of solution IV and 0.03 ml of solution V were mixed and kept at 25° C. for 5 minutes. Then 0.1 ml of solution III was added, mixed and the alteration of extinction was determined spectrophotometrically at 366 nm for 3 minutes.

Determination of inhibition of incubation 0.1 ml of solution I, 0.1 ml of solution II, 2.67 ml of solution IV and 0.03 ml of solution V were mixed and kept at 37° C. for 60 minutes. Then 0.1 ml of solution III was added, mixed and the alteration of extinction was measured spectrophotometrically at 366 nm for 3 minutes.

The inhibitory values were calculated from the average values of three measurements (alteration of extinction per minute) compared with controls, which received the pure solvent as the inhibitory solution. Then the ED50 was calculated according to Reed and Muench from the inhibitory values for the various concentrations.

The following table contains the results:

TABLE III

| | G6PDH-inhibition ED$_{50}$ [µg/ml] | |
|---|---|---|
| Substance | Immediate Inhibition | Inhibition of Incubation |
| A | >50 | 33 |
| B | 34.5 | 30 |
| C | 37.5 | 20 |
| D | >50 | >50 |

Measurement of the inhibition of cell cultures

Method

HeLa-cell culture was treated with trypsin and adjusted to a cell number of 150,000 cells/ml of fresh medium. The substance was always dissolved in the same quantity of dimethyl sulfoxide and then further diluted with growth medium. 0.1 ml of the substance-dilutions were added to each well of microtiter plates and then 0.2 ml of cell suspension were added (4 wells per dilution). Several growth controls containing 0.1 ml of growth medium instead of 0.1 ml of substance dilution were put up. After careful mixing, the cultures were incubated at 37° C. for 3 days in a 5% carbon dioxide atmosphere. The reading was effected in comparison with these controls. The results were given as the percentage of the deficiency and degeneration compared to the growth control. The minimal inhibitory concentration was determined from these results and the ED50 was calculated according to Reed and Muench. The data are referred to µg of substance per ml of total medium.

The results are recorded in the following table:

TABLE IV

| Substance | Minimal inhibitory concentration µg/ml | ED$_{50}$ µg/ml |
|---|---|---|
| A | 3.13 | 12.5 |
| B | 6.25 | 9.75 |
| D | 25 | 90.1 |

The mentioned compounds are chemically stable, show a good lipophilic behavior (distribution-coefficient n-octanol/water >1000) and may well be incorporated into ointments, creams, tinctures, sprays, powders etc., which are suitable for topical application.

The good compatibility on the skin (a cream containing 10% of compound A was tolerated without irritation for over 24 hours under occlusion) and the low toxicity are of special advantage.

The acute toxicity was determined with mice. The LD50, the dose leading to the death of 50% of the animals within 14 days, was calculated. LD50 in the mouse:

| Compound A | i.p. | 105 mgm/kg |
|---|---|---|

| | | |
|---|---|---|
| Compound B | i.p. | 88 mgm/kg |

In the general pharmacological screening of the substances, which indicates an influence on essential body functions, e.g. heart/circulation or central nervous system, no significant effects were shown. Systemic side-effects are, therefore, not expected with local applications.

Because of the good lipophilic behavior at simultaneous presence of polar groups the compounds penetrate well into the skin, however, they are only resorbed to a small extent as could be shown by analysis of the excretion.

The examination on the compatibility on the skin and sensitization, which were carried out with guinea pigs, showed that the weakly sensitizing properties of some resorcins disappear by the introduction of the trifluoroacetyl group. A resorcins such as hexylresorcinol in some cases cause allergies in humans, this is a considerable advantage.

At present an effective therapy of acne is only possible systemically with strong antibiotics (tetracycline, erythromycine) and locally with peeling agents such as a vitamin-A-acid and benzoyl peroxide. The application of antibiotics for a disease by no means endangering life is problematic in principle because of the resistance formation, when peeling agents are applied one must expect considerable irritation of the skin.

In the acne-therapy with antibiotics the gram-positive bacteria important for acne, above all Corynebacterium acnes, are diminished, which leads to a reduction of the content of free fatty acids, which were split off from triglycerides by these bacteria, in the sebum.

As table I show, the above-mentioned compounds are strongly active against Corynebacterium acnes. In addition, it could be shown that after local application a considerable reduction of the content of free fatty acids is possible. Thus, a *local* therapy is possible, which may be compared in its effect with the *oral* therapy with antibiotics.

The exact cause of dandruff formation is unknown up to now. However, a hyperkeratosis may be found with dandruff, i.e. mitosis in the epidermis is accelerated; additionally the hyperkeratosis is distributed. According to the statements of some authors, e.g. R. A. Gosse, R. W. VanderWyck, J. Soc. Cosmet. Chem. 20, 603 (1969), the yeast *Pityrosporum ovale* plays a role for the genesis of dandruff.

Table II shows that some of the above-mentioned compounds have a strong effect against *Pityrosporum ovale*.

It may be seen in tables III and IV that these and other compounds can delay accelerated mitosis processes. thus, a therapy of dandruff is possible with compounds showing a good activity in tables II, III and IV.

At present an effective therapy of psoriasis is only possible topically with dithranol, tar preparations and highly active corticoides and systemically with antimetabolites such as methothrexate, corticosteroids and cytostatics. Additionally, the physical treatment with UV-light, X-rays and the combined application of psoralens (systemically and locally) and UV-light are used. All these treatment methods are either circumstantial or accompanied by considerable side-effects. Therefore, a simple effective local therapy is of advantage. Tables III and IV show that some of the above-mentioned compounds may be used for psoriasis-therapy.

Mycoses of the skin are becoming more frequent. As the kind of microorganism causing an irritation often cannot be determined, the application of broad spectrum antimycotics against dermatophytes, yeasts and bacteria is of special advantage.

Tables I and II show that the above-mentioned compounds are strongly active against these microorganisms and may, therefore, be used for therapy of mycoses and bacterial skin infections.

Additionally, the compounds have a conserving effect on the usual cosmetic preparations by preventing the settlement of microorganisms.

The following examples serve to illustrate the invention.

The compounds of the formula I may be incorporated into the usual pharmaceutical and cosmetic preparations, e.g. foam aerosols, powder sprays, powders, throat sprays, shampoos, creams, ointments, tinctures, pastes or gels. The dosage of the active substances is between 1 and 10% by weight, preferably 1.5 to 5% by weight. For cosmetic preparations a smaller dosage is sufficient, generally between 0.1 and 3% by weight.

EXAMPLE 2

| Foam aerosol (filling/can : 60 gm) containing 3% by weight of 2,4-dihydroxy-3-ethyl-trifluoroacetophenone | |
|---|---|
| (quickly breaking foam) | |
| Active ingredient | 1.80 gm |
| Cremophor EL = reaction product of castor oil with ethylene oxide (1 mol : 40 mols) | 0.50 gm |
| Tween 80 = polyethoxylated sorbitanmonooleate | 0.80 gm |
| Texapon N 25 = sodium lauryl ether sulfate | 0.50 gm |
| French brandy essence | 0.25 gm |
| Ethanol 96% | 12.75 gm |
| Water | 35.00 gm |
| Propellant mixture ad (Frigen 12/114 in the proportion of 60:40 parts by volume) | 60.00 gm |

(a) Solution of active ingredient

The active ingredient, Cremophor EL and the French brandy essence were successively dissolved in ethanol at room temperature.

Tween 80 and Texapon N 25 were dissolved in water, also at room temperature, combined with the ethanolic solution and filtered.

(b) Preparation of aerosol 51.6 gm of the solution of active ingredient were filled into an alu-monobloc can of suitable size provided in the inside with a double protecting coat of lacquer. The can closed with a valve was subsequently filled with 8.4 gm of propellant mixture by means of propellant filling equipment.

EXAMPLE 3

| Powder spray (filling/can : 100 gm) containing 2% by weight of 2,4-dihydroxy-3-ethyl-trifluoroacetophenone | |
|---|---|
| Active ingredient | 2.00 gm |
| Aerosil (colloidal silicic acid) | 0.50 gm |
| ANM-maize (corn starch) | 2.00 gm |
| Isopropyl myristate | 0.50 gm |
| Propellant mixture ad (Frigen 11/12 in the proportion | 100.00 gm |

-continued

| Powder spray (filling/can : 100 gm) containing 2% by weight of 2,4-dihydroxy-3-ethyl-trifluoroacetophenone |
| --- |
| of 50:50 parts by volume) |

(a) Powder of active ingredient

The active ingredient was ground in a pinned disk mill together with Aerosil and corn starch and triturated with the isopropyl myristate in a mortar.

(b) Preparation of aerosol 5 gm of the powder of active ingredient were filled into an alu-monobloc can of suitable size. The can closed with a valve was subsequently filled with 95 gm of propellant mixture by means of a propellant filling equipment.

EXAMPLE 4

| Powder containing 3% by weight of 2,4-dihydroxy-3-ethyl-trifluoroacetophenone | |
| --- | --- |
| Active ingredient | 3.00 gm |
| Aerosil 200 | 0.50 gm |
| Magnesium stearate | 0.20 gm |
| Lactose | 48.80 gm |
| ANM-maize (corn starch) | 48.00 gm |

The micronized active ingredient was mixed with Aerosil 200, magnesium stearate, lactose and corn starch and subsequently ground in a pinned disk mill.

EXAMPLE 5

| Throat spray containing 1.5% by weight of 2,4-dihydroxy-3-ethyl-trifluoroacetophenone | | |
| --- | --- | --- |
| Active ingredient | | 1.50 gm |
| Glycerin | | 20.00 gm |
| Sodium saccharin | | 0.02 gm |
| Ethanol 96% | | 10.00 gm |
| Cremophor RH 40 = reaction product of hydrogenated castor oil with ethylene oxide | | 1.00 gm |
| Menthol 42–44° C. | | 0.05 gm |
| Aroma | | 0.04 gm |
| Dyestuff blue | | q.s. |
| Distilled water | ad | 100.00 gm |

The active ingredient was dissolved in ethanol together with methanol and aroma and subsequently glycerin was added. In a portion of the water Cremophor RH 40, sodium saccharin and dyestuff were dissolved successively, this solution was combined with the ethanol-glycerin solution, filled up with water and filtered. Spraying is effected by means of a mechanical pump dosing valve.

EXAMPLE 6

| Shampoo containing 1.5% by weight of 2,4-dihydroxy-3-ethyl-trifluoroacetophenone | |
| --- | --- |
| Active ingredient | 1.50 gm |
| Comperlan KD = coconut fatty acid diethanol-amide | 3.00 gm |
| Zetesol 856 T = fatty alcohol ether sulfate | 25.00 gm |
| Lamepon S-TR = condensation product of protein hydrolyzates with vegetable fatty acids | 5.00 gm |
| Euperlan PK 771 = fatty alcohol ether sulfates | 10.00 gm |
| Cetiol HE = polyol fatty acid esters | 2.50 gm |

-continued

| Shampoo containing 1.5% by weight of 2,4-dihydroxy-3-ethyl-trifluoroacetophenone | |
| --- | --- |
| Chemoderm = perfume oil composition | 0.50 gm |
| Dyestuff (yellowish orange 11963) | 0.012 gm |
| Nip/Nip (8/2) = methyl-p-hydroxybenzoate + n-propyl-p-hydroxy-benzoate | 0.20 gm |
| Distilled water ad | 100.00 gm |

Nipagine/Nipasol (Nip/Nip) were dissolved in a portion of the water while heating, subsequently Comperlan, Zetesol 856 T, Lamepon S-TR, Euperlan, Cetiol HE and dyestuff were successively stirred in at room temperature.

After addition of the active ingredient and homogenizing well the perfume was added.

EXAMPLE 7

| Gel containing 3% by weight of 2,4-dihydroxy-3-ethyl-trifluoroacetophenone | | |
| --- | --- | --- |
| Active ingredient | | 3.00 gm |
| Tween 80 = polyethoxylated sorbitan-mono-oleate | | 0.10 gm |
| Carbopol 940 = acrylic acid polymerisate | | 0.75 gm |
| Nip/Nip (8/2) | | 0.30 gm |
| Silicone oil AK 350 | | 3.00 gm |
| Triethanolamine solution 10% | | 3.70 gm |
| Water | ad | 100.0 gm |

Nipagine and Nipasol were dissolved in a portion of the water while heating, and Carbopol was added at about 50° C. while stirring vigorously.

The micronized active ingredient was suspended in the remaining water, mixed with Tween, and added to the Carbopol suspension. Subsequently the silicone oil was stirred in and the viscosity was adjusted while further stirring with triethanolmaine.

EXAMPLE 8

| Cream with 5% by weight of 2,4-dihydroxy-3-ethyl-trifluoro-acetophenone | |
| --- | --- |
| Active ingredient | 5.0 gm |
| Isopropyl myristate | 7.0 gm |
| Silicone oil AK 350 | 0.5 gm |
| Tween 60 | 2.0 gm |
| Span 60 | 2.0 gm |
| Lanette 0 | 7.0 gm |
| Propylene glycol 1.2 | 7.0 gm |
| Nip/Nip (8/2) | 0.3 gm |
| Distilled water | 69.2 gm |

Isopropyl myristate, silicone oil, Tween, Span and Lanette were melted at 75° C. and kept at this temperature. Propylene glycol, Nip/Nip (8/2) and water were boiled for a short time and cooled to 75° C. The active ingredient was stirred into the isopropyl myristate melt; this mixture was stirred into the propylene glycol mixture, the finished mixture was allowed to cool.

The compounds of the formula I may also be used as active ingredients in pesticides, especially for the control of phytopathogenic fungi.

There is to be stressed the use of the compounds as active ingredients of compositions for seed-treatment. These compositions are very effective against damping off diseases in plant cultures, e.g. against fungi of the genera tiletia, helmintosporium, ustilago and fusarium. Besides there is to be mentioned the herbicidal effect of the compounds, which therefore may be used as total herbicides. On the other hand they may be used selectively against undesired monocotyledons, such as wild oats, and against weeds (dicotyledons) in cereal and other plant cultures.

For use in plant protection the compounds according to formula I are processed to conventional formulations, especially to solution- or emulsion-concentrates, dusts, granulates, spray powders, seed-treatment powders and -solutions. The content of active substance in the sprays and dusts amounts to 0.01 to approximately 3% by weight. The seed-treatment solutions (approximately 10 to 50% by weight) and seed-treatment powders (approximately 20 to 90% by weight) as well as the concentrates (up to approximately 95% by weight) comprise higher concentrations of active substance.

Examples for formulation:

1. Suspension Powder:

30 parts by weight of a compound of formula I
9 parts by weight of sodium lingine sulfonate
1 part by weight of sodium naphthaline sulfonate
60 parts by weight of colloidal silicic acid The components are ground homogeneously. For use as an herbicide there is produced an aqueous spray with a content of active ingredient of 0.01 to 3% by weight. The spray may be used for the control of undesired monocotyledons, such as wild oats, as well as weeds (dicotyledons) in cereal and other cultures. When applying higher doses, the use as total herbicide is possible too.

The other compounds of formula I may be used in a corresponding way.

2. Seed-treatment Solution 20 parts by weight of a compound of formula I
79 parts by weight of dimethylformamdie 3. Seed-treatment Powder 80 parts by weight of a compound of formula I
3 parts by weight of magnesium stearate
17 parts by weight of talcum The other compounds of formula I may be used in a corresponding manner.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of inhibiting the growth of bacteria and fungi, which comprises contacting said bacteria and fungi with an effective amount of a composition consisting essentially of an inert pharmaceutical carrier and from 1 to 10% by weight, based on the total weight, of at least one compound selected from the group consisting of 2,4-dihydroxy-trifluoroacetophenone, 5-ethyl-2,4-dihydroxy-trifluoroacetophenone and 3-ethyl-2,4-dihydroxy-trifluoroacetophenone.

* * * * *

UNITED STATES PATENT AND TRADEMARK OFFICE
CERTIFICATE OF CORRECTION

PATENT NO. : 4,229,479
DATED : October 21, 1980
INVENTOR(S) : ROLF BRICKL ET AL.

It is certified that error appears in the above—identified patent and that said Letters Patent is hereby corrected as shown below:

Column 2, line 36: "triflouride" should read -- trifluoride --.

Column 4, line 13: "Sodium chloride      gm" should read -- Sodium chloride    1 gm --.

line 15: "5-14 10 minutes" should read -- 5-10 minutes --.

Column 5, line 8: "addad" should read -- added --.

Column 7, line 23: After "NADPH + $H^+$" insert the following line:

-- (NADP = nicotinamide-adenine-dinucleotide-phosphate, G6P-DH = gluconic acid-6-phosphate-dehydrogenase). --

Column 9, line 20: "A" should read -- As --.

line 56: "thus" should read -- Thus --.

UNITED STATES PATENT AND TRADEMARK OFFICE
CERTIFICATE OF CORRECTION

PATENT NO. : 4,229,479

DATED : October 21, 1980

INVENTOR(S) : ROLF BRICKL ET AL.

It is certified that error appears in the above—identified patent and that said Letters Patent is hereby corrected as shown below:

Column 14, line 6: "dimethylformamdie" should read -- dimethylformamide --.

Signed and Sealed this

Thirtieth Day of December 1980

[SEAL]

Attest:

SIDNEY A. DIAMOND

Attesting Officer

Commissioner of Patents and Trademarks